(12) United States Patent
Lorraine

(10) Patent No.: US 6,182,512 B1
(45) Date of Patent: Feb. 6, 2001

(54) METHOD AND APPARATUS FOR IMAGING THIN STRUCTURES

(75) Inventor: Peter William Lorraine, Niskayuna, NY (US)

(73) Assignee: General Electric Company, Schenectady, NY (US)

(*) Notice: Under 35 U.S.C. 154(b), the term of this patent shall be extended for 0 days.

(21) Appl. No.: 08/876,175

(22) Filed: Jun. 13, 1997

(51) Int. Cl.⁷ .................................................. G01N 21/00
(52) U.S. Cl. .................................................. 73/655; 73/602
(58) Field of Search .......................... 73/655, 656, 657, 73/625, 626, 602; 356/357, 358

(56) References Cited

U.S. PATENT DOCUMENTS

| | | | |
|---|---|---|---|
| 4,387,597 | * 6/1983 | Brandestini | 73/626 |
| 5,027,658 | * 7/1991 | Anderson | 73/626 |
| 5,501,222 | * 3/1996 | Briggs | 73/624 |
| 5,604,592 | 2/1997 | Kotidis et al. | |
| 5,760,904 | * 6/1998 | Lorraine et al. | 356/360 |
| 5,801,312 | * 9/1998 | Lorraine et al. | 73/602 |
| 5,835,199 | * 11/1998 | Phillips et al. | 356/5.03 |

OTHER PUBLICATIONS

Lance E. Rewerts et al., *Dispersion Compensation in Acoustic Emission Pipeline Leak Location*, 16A Review of Progress in Quantitative Nondestructive Evaluation 427–434 (1997).

R.C. Addison, Jr. et al., *Laser–based Ultrasound for the Inspection of Gas Pipelines*, 16B Review of Progress in Quantitative Nondestructive Evaluation 1277–1284 (1997).

Y. Nagata et al., *Lamb Wave Tomography Using Laser–Based Ultrasonics*, 14A Review of Progress in Quantitative Nondestructive Evaluation 561–568 (1995).

Jean–Pierre Monchalin, *Progress Toward the Application of Laser–Ultrasonics in Industry*, 12A Review of Progress in Quantitative Nondestructive Evaluation 495–506 (1993).

A.D. McKie and R.C. Addison, Jr., *Rapid Inspection of Composites Using Laser–Based Ultrasound*, 12A review of Progress in Quantitative Nondestructive Evaluation 507–516 (1993).

Christian Padioleau et al., *Laser Ultrasonic Inspection of Graphite Epoxy Laminates*, 12B Review of Progress in Quantitative Nondestructive Evaluation 1345–1352 (1993).

Yoshihiko Ozaki et al., *A New System for Real–Time Synthetic Aperture Ultrasonic Imaging*, 35 IEEE Transactions on Ultrasonics, Ferroelectrics, and Frequency Control 828–838 (1988).

George L. Turin, *An Introduction to Matched Filters*, IRE Transactions on Information Theory 311–329 (1960).

* cited by examiner

*Primary Examiner*—Hezron Williams
*Assistant Examiner*—Nashmiya Fayyaz
(74) *Attorney, Agent, or Firm*—Patrick K. Patnode; Marvin Snyder

(57) ABSTRACT

An exemplary imaging apparatus includes a wave generator for generating a wave in an article; a detector for detecting a wave in the article; and a processor which: forms a matched filter based on a response of the article to a wave propagated through the article; directs the wave generator to generate a wave at a plurality of generation positions; directs the detector to detect a motion of the article at a plurality of detection positions; forms a scan data set from the detected motion of the article; multiplies the scan data set by the matched filter to produce a compensated data set; and coherently sums data points in the compensated data set to produce a focused image.

29 Claims, 5 Drawing Sheets

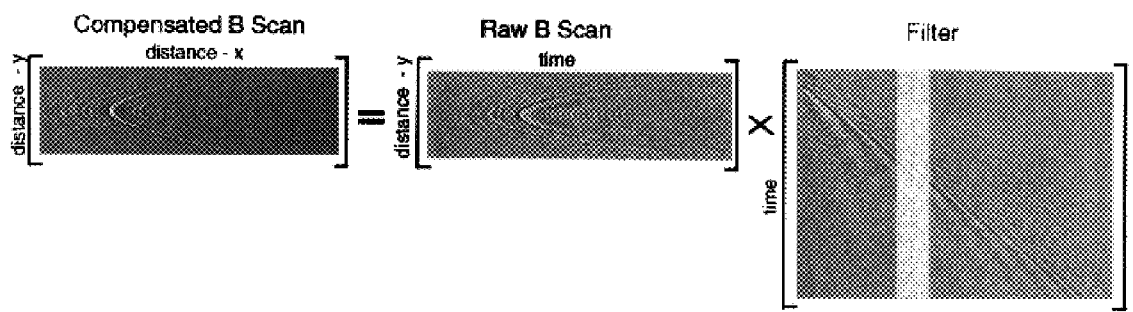
*FIG. 4a*   *FIG. 4b*   *FIG. 4c*

METHOD AND APPARATUS FOR IMAGING THIN STRUCTURES

The government may have certain rights in this invention pursuant to contract no. F33615-94-2-4439 awarded by the U.S. Department of Defense.

BACKGROUND

1. Field of the Invention

The present invention relates generally to non-destructive evaluation, and more particularly to a method and apparatus for laser ultrasound inspection of materials with synthetic aperture focusing.

2. Description of the Related Art

Laser ultrasound involves the generation or detection of ultrasound in materials with lasers. Generally, in laser ultrasound, a source laser irradiates a material with a laser beam along its surface. Ultrasonic waves are generated by the laser beam by non-destructive local heating of the surface to create expansion and a strain wave, or by increasing the amplitude of the beam to vaporize a small amount of material to form a plasma that strikes the surface like a hammer.

The ultrasonic wave propagates throughout the material and is reflected back to the surface of the material. As the reflected ultrasonic wave returns to the surface of the material, typically an interferometric detector is used to detect either displacement or velocity at the surface by irradiation of the surface with another laser beam. The detected displacement or velocity signals are used to generate an image of the material. A more detailed discussion on laser ultrasound is provided in C. B. Scruby et al., *Laser Ultrasonics-Techniques and Applications* (IOP Publishing Ltd. 1990), which is hereby incorporated by reference.

When laser ultrasound is used to inspect thin structures, image resolution generally decreases because Lamb waves are generated. Lamb waves are generated when the object being imaged is less than several wavelengths thick, as surface waves engage the thin structure on its opposing face. Lamb waves are dispersive, which means that different frequency components of the Lamb wave propagate with different velocities. The dispersive characteristic of Lamb waves results in decreased image resolution, since the arrival time of the reflected wave is less well defined.

Although it is possible to compensate for frequency dispersion in Lamb waves through modeling, this technique involves considerable analytical effort. In addition, where multiple modes of propagation exist, it is analytically difficult to model all modes accurately. These problems are compounded in anisotropic materials in which the wave speed is dependent on propagation direction.

It would be desirable, therefore, to have a method and apparatus for accurately and efficiently imaging a thin structure using laser ultrasound.

SUMMARY

A method for forming an image of an article, according to an exemplary embodiment of the invention, comprises the steps of forming a matched filter data set comprising first data points representing a response of the article as a function of a distance to a source; generating waves in the article at a plurality of generation positions on the article, which waves propagate through the article; detecting a motion of the article at a plurality of detection positions to obtain second data points, the second data points forming a scan data set; multiplying the scan data set by the matched filter data set to generate a compensated data set comprising a plurality of third data points; and coherently summing the third data points in the compensated data set to form an image of the article.

An exemplary apparatus comprises a wave generator for generating a wave in an article; a detector for detecting a wave in the article; and a processor which: forms a matched filter based on a response of the article to a wave propagated through the article; directs the wave generator to generate a wave at a plurality of generation positions; directs the detector to detect a motion of the article at a plurality of detection positions; forms a scan data set from the detected motion of the article; multiplies the scan data set by the matched filter to produce a compensated data set; and coherently sums data points in the compensated data set to produce a focused image.

The exemplary method and apparatus are particularly suitable for inspection and imaging aircraft skins which are typically formed of curved sheets of metal, riveted to adjoining panels and supporting structure. As aircraft age, the skins need to be inspected for cracks, disbonds, corrosion, and other defects. The large areas to be inspected, as well as curved or layered structures, can be efficiently and accurately inspected with exemplary embodiments of the invention.

BRIEF DESCRIPTION OF THE DRAWINGS

Other features and advantages of the invention will be more readily understood upon reading the following detailed description, in conjunction with the drawings, in which:

FIGS. 4*a*–4*c* graphically illustrate compensation of scan data with a matched filter;

DETAILED DESCRIPTION OF THE PREFERRED EMBODIMENTS

Figure 1:
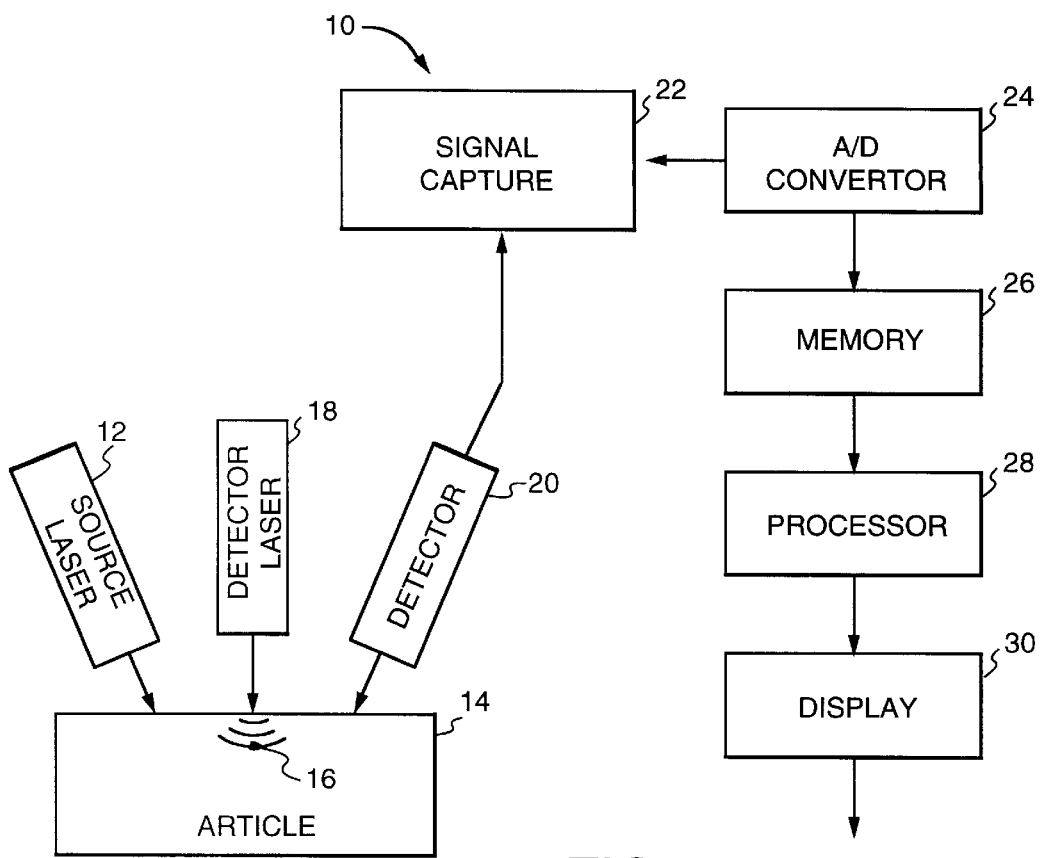
FIG. 1 is a diagram of an imaging apparatus according to an exemplary embodiment of the invention.

FIG. 1 shows a block diagram of a laser ultrasound inspection system 10 according to an exemplary embodiment of the invention. In the laser ultrasound inspection system 10, a source laser 12 is scanned over the surface of an article 14 with a suitable conveyor. The article may be an engineering material such as a metal aircraft skin, for example. The source laser 12 irradiates the article 14 with a laser beam along its surface at a plurality of scanning positions. The laser beam generated from the source laser 12 typically has a relatively high energy, for example on the order of $5 \times 10^8$ W/cm$^2$ or less. Ultrasonic waves are generated by the laser beam either by non-destructive local heating of the surface to create expansion and a strain wave (thermoelastic generation) or by increasing the amplitude of the beam to vaporize a small amount (e.g., <1 micron) of material to form a plasma that strikes the surface like a hammer (ablation generation). A third approach involves laser heating of a surface coating, such as an oil film or paint, to generate sound through thermoelastic generation or ablation generation. In the illustrative embodiment, the generated ultrasonic waves are either surface or Lamb waves.

The generated ultrasonic waves propagate through the article 14 and are reflected back to the scanning position by a reflector 16 such as a defect located within the article or along the surface of the article. As the reflected ultrasonic waves return to the scanning position, a detection laser 18 is used to detect either displacement or velocity at the surface by simultaneously irradiating the surface of the article with another laser beam. The laser beam generated from the detection laser 18 has line width, stability, and fluence suitable for interferometric detection. A detector 20, typically a sensitive interferometric detector, detects and amplifies the displacement or velocity signals and outputs the signals to a signal capture 22.

The amplified signals, which represent laser ultrasound waveform data, are digitized by an AND converter 24 and stored in a memory 26. The laser ultrasound waveform data stored in the memory 26 form a scan data set comprising a plurality of data points which represent a motion of the article, such as surface displacement or velocity, as a function of time or frequency, at a plurality of detection points. The scan data set stored in the memory is processed by a processor 28. The processor reconstructs an image of the article that may be displayed on a display 30.

The sensitivity of laser ultrasound imaging can be significantly improved with the synthetic aperture focusing technique (SAFT). The laser detector 20 itself is typically sensitive only to the normal component of motion and does not differentiate between different directions of arrival of the reflected ultrasonic waves. The laser detector 20 is thus unable to focus and therefore identify the exact spatial location of any reflectors 16 within the article 14 which give rise to the detected signals. In synthetic aperture focusing, however, reflected signals obtained at different scan positions are coherently summed by delaying each signal a specified time period to focus the reflected signal which diverges from the reflector 16. Synthetic aperture focusing allows the signals reflected in different directions from the reflector to be synthetically focused to produce an image with improved resolution.

Figure 2A:
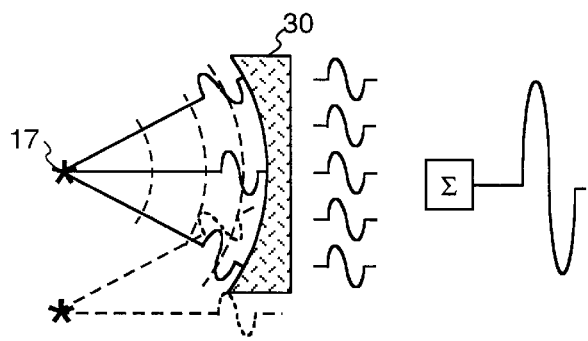
FIG. 2*a* illustrates focusing using a conventional physical transducer.
Figure 2B:
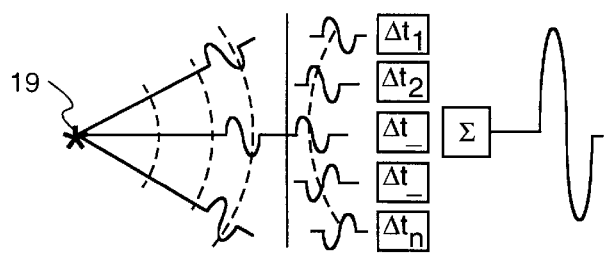
FIG. 2*b* illustrates the synthetic aperture focusing technique (SAFT)

FIGS. 2a and 2b illustrate methods of focusing waves reflected from a reflector 16. As shown in FIG. 2a, a physically focused transducer 30 sums wavefronts arriving across the face of the transducer, which may comprise a piezoelectric material. A coherent sum is produced for signals arriving in phase from a localized region 17 (the focus), and an incoherent sum is produced for other signals. The physical focus can be realized either with a shaped lens or with a shaped transducer element.

FIG. 2b illustrates the synthetic aperture focusing technique (SAFT). In FIG. 2b, a generalized or synthetic transducer is formed by creating arbitrary delays to move the focal point 19 about. The synthetic aperture focusing technique may utilize a single transmitter with a diverging beam and a single receiver which are scanned across the surface of the article to cover the desired aperture. The transducer location and the speed of sound through the article are used to create a focused image. The image in SAFT is formed by summing the detected waveforms U(xj, yj, zj, t) across the reception aperture j:

$$I(x_i, y_i, z_i) = \sum_j U(x_j, y_j, z_j, \Delta t_{ij}) \qquad (1)$$

where $\Delta t_{ij}$ is the round trip time delay for sound propagation from the observation point (xj, yj, zj) to the image point (xi, yi, zi). In isotropic materials, $\Delta t_{ij}$, is given by:

$$\Delta t_{ij} = \frac{1}{2}[(x_i - x_j)^2 + (y_i - y_j)^2 + (z_i - z_j)^2]^{1/2} / v_{material}, \qquad (2)$$

where $V_{material}$, is the speed of sound in the material. Time delays are calculated for each focal position so SAFT may focus at any location in three dimensions, whereas a physical transducer focuses only at a single position.

Ultrasonic surface waves, e.g., Rayleigh and Lamb waves, travel extended distances when the article is not immersed. With SAFT, this information can be used to make images of the article outside the immediate scan area. A large area can be imaged from a single scan line, resulting in an enormous gain in effective scan rate, e.g. greater than 100 times. Application of SAFT to laser ultrasound surface wave data thus permits formation of high resolution images across extended areas or volumes.

Figure 3A:
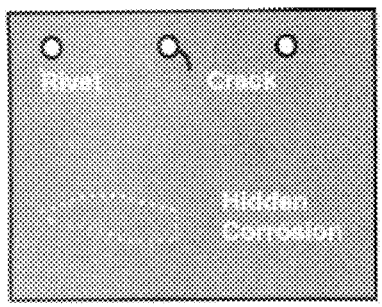
FIGS. 3*a*–3*c* illustrate synthetic aperture focusing of an extended area from a single line of scan points.
Figure 3B:
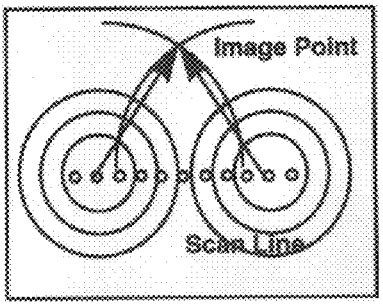
Figure 3C:
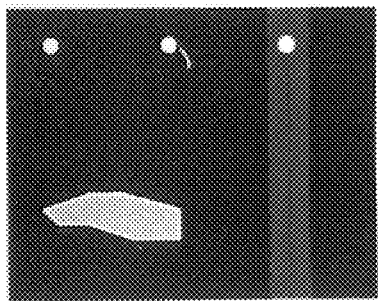

FIGS. 3a–3c illustrate the application of SAFT to a line of scan data points. FIG. 3a illustrates an article with cracks and hidden corrosion. FIG. 3b shows a scan line which covers a limited area. FIG. 3c shows an image reconstructed with SAFT, illustrating that the limited area scan line can produce an image over a much larger area.

Although the synthetic aperture focusing technique (SAFT) provides a significant improvement in image resolution, image resolution can be adversely affected when imaging thin structures such as aircraft skins. Surface waves typically extend down into the article a distance on the order of twice the surface wavelength. When the depth of the wave approaches the part thickness, as in the case of sheet materials such as aircraft skins, interaction with the opposite boundary of the article modifies the wave behavior giving rise to Lamb waves. Lamb waves are dispersive in frequency, i.e., different frequencies of sound propagate with different velocities. A Lamb wave at one location therefore produces a dispersed waveform at a remote location. In addition, multiple Lamb wave modes, for example symmetric and antisymmetric modes, may exist, which propagate with different dispersion relations. Direct application of SAFT to surface wave data in thin plates can thus produce images of compromised resolution due to frequency dispersion and multiple mode propagation which result in a range of arrival times for the various wave components. Because different components of the Lamb wave propagate at different velocities, the focal position cannot be well defined. Application of SAFT in the time domain, for example, may focus only a narrow range of frequencies well.

Exemplary embodiments of the invention provide an improved image by compensating for frequency dispersions and multiple Lamb wave mode propagation produced in thin parts. Dispersion compensation may be achieved with a matched filter which represents an idealized waveform response for different propagation distances. The matched filter, according to an exemplary embodiment, comprises a set of data points which represent a response of the article, such as surface displacement or velocity, over time or frequency, as a function of distance from the source of the wave. The matched filter may be constructed by empirically measuring the surface displacement or velocity over time or frequency at a number of arbitrary scan positions $r_0, r_1, \ldots, r_m$. For example, according to one embodiment, a "one-way" matched filter may be constructed by holding the source laser 12 of FIG. 1 fixed while measuring surface displacement or velocity as a function of time or frequency with the detector laser 18 and detector 20 at a number of scan positions which are at different distances from the source laser 12.

According to another embodiment, a "pulse-echo" matched filter may be constructed by propagating a wave with the source laser 12 to a reflector 16 and measuring the response (e.g. surface displacement or velocity) of the article 14 based on the reflected wave with the detector laser 18 and detector 20. The source laser 12 may generate waves at a plurality of generation positions which may or may not correspond with a plurality of detection positions at which the detector laser 18 and detector 20 measure the response of the article.

Because the pulse echo matched filter is constructed using a particular type of reflector, the pulse echo matched filter may be constructed to be particularly sensitive to a desired type of reflector. Since each reflector has particular reflection characteristics, a matched filter constructed with a desired type of reflector (e.g., a simulated 3 mm crack) will exhibit a greater degree of correlation with similar reflectors (e.g. an actual 3 mm crack) than with other types of reflectors (e.g. corrosion). Thus, the pulse echo matched filter can be constructed to be more sensitive to certain types of defects.

The matched filter may also be constructed analytically, with a model of the frequency dispersion which occurs as a wave propagates through a thin structure. The model is used to calculate the data points which make up the matched filter data set. For example, analytical methods may be used to solve for the wave dispersion relations based on acoustic wave equations, the elastic properties of the material, and boundary conditions. Given a model pulse, the dispersion relations may be used to forward propagate the pulse to arbitrary distances, resulting in a data set for use as a matched filter. An analytical pulse-echo matched filter can also be constructed by modeling the reflective characteristics of a desired type of defect.

An example of a matched filter, which typically comprises a matrix of data points, is shown graphically in FIG. 4c. The data shown in FIGS. 4a through 4c were obtained by focusing a pulsed neodymium:yttrium-aluminum-garnet (Nd:YAG) laser with an axicon lens to produce a ring of light on the surface of a 0.02 inch thick sheet of aluminum. A confocal Fabry-Perot receiver was scanned on the opposite side of the aluminum to produce the one-way matched filter shown in FIG. 4c. In FIG. 4c, the brightness of each pixel represents surface velocity. The downwardly sloping line represents the arrival of the wave generated by the fixed source laser 12 at different distances from the source laser. As the distance from the source laser increases, the wave arrival is later in time. The data points of the matched filter shown in FIG. 4c also contain information describing the dispersion of the wave as a function of propagation distance from the source laser 12.

After the matched filter has been constructed for a suitable sample of material, the article to be imaged is scanned. A scan data set is typically obtained by scanning the source laser 12, the detector laser 18, and the detector 20 together at a number of scan positions on the article 14, for example as shown in FIG. 3. Each point in the scan data set represents a motion of the article, for example a surface displacement or velocity, at a particular detection position, at a particular frequency or time. The wave generated by the source laser 12 may be reflected off a defect 16, for example, back to the surface of the article 14. The travel time for the reflected wave depends on the position of the defect 16 with respect to the source laser 12 and detector laser 18. The scan data set, therefore, contains information on the proximity of defects with respect to each detection position.

In FIG. 4b, the scan data set was obtained by scanning only the detector laser 18 and detector 20 (without the source 12), since the source laser 12 was used at an unknown distance to simulate a defect in the article to be imaged. FIG. 4b depicts graphically the scan data set containing unknown waveforms. As shown in FIG. 4b, the exemplary scan data set comprises a hyperbolic curve, modified by dispersion and the presence of multiple modes, in which the shortest arrival time is approximately in the middle scan position along the y-axis. This curve indicates that the source laser 12, used to simulate a defect in the article, was positioned approximately opposite the middle scan position on the article.

Matrix multiplication of the unknown waveforms represented by the scan data set by the matched filter produces a waveform matrix with dispersion removed. For a typical laser ultrasound imaging embodiment, multiple waveforms are acquired for a range of positions $y_0, y_1, \ldots, y_n$, corresponding to the scan positions shown in FIG. 3. The resulting matrix of scan data is multiplied by the filter to obtain the compensated data:

$$\begin{bmatrix} U(y_0, r_0) & \cdots & Uy_0, r_m) \\ \vdots & \vdots & \vdots \\ U(y_n, r_0) & \cdots & U(y_n, r_m) \end{bmatrix} = \begin{bmatrix} u(y_0, t_0) & \cdots & u(y_0 t_m) \\ \vdots & \vdots & \vdots \\ u(y_n, t_0) & \cdots & u(y_n t_m) \end{bmatrix} \quad (3)$$

$$\begin{bmatrix} f(t_0, r_0) & \cdots & f(t_0, r_m) \\ \vdots & \vdots & \vdots \\ f(t_n, r_0) & \cdots & f(t_n, r_m) \end{bmatrix}$$

where $f(t_n, r_m)$ represents a data point in the matched filter, $U(y_n, t_m)$ is a data point of the measured waveform, and $U(y_n, r_m)$ is a data point in the compensated data set. Equation (3) is represented graphically in FIGS. 4a through 4c.

The uncompensated scan data of FIG. 4b show complex dispersion and phase wrapping, including alternating positive and negative components for a single mode of propagation as a function of distance. Multiple modes are also evident. The compensated data of FIG. 4a, by contrast, show a single clear, bright arrival. The matched filter shown in FIG. 4c, according exemplary embodiments of the invention, compensates rigorously for dispersion and propagation of multiple modes.

Another advantage of exemplary embodiments of the invention is that the matched filter produces a compensated data set of spatial rather than temporal data. It is therefore not necessary, when focusing the data with SAFT, to estimate the velocity of sound through the article, because the data is indexed to distance rather than time. Equation (2) can thus be modified to eliminate the variable $V_{material}$. Coherent summing involves calculating an adjusted distance, rather than a time delay, from each observation point to the focal point, and summing data points at adjusted distances which are about equal. Because the position of the focal point can be arbitrarily defined, SAFT can be used to focus any region of the article being imaged.

Figure 5A:
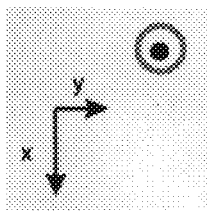
FIG. 5*a* represents an ideal reconstructed image using SAFT.
Figure 5B:
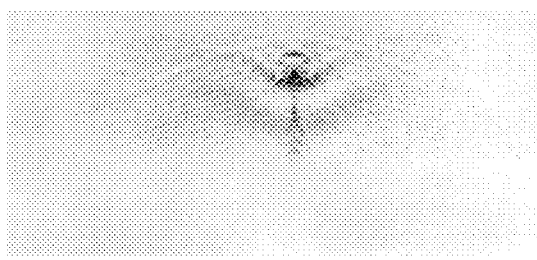
FIG. 5*b* illustrates a SAFT reconstructed image without a matched filter.
Figure 5C:
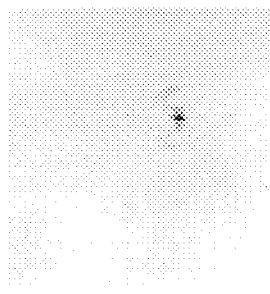
FIG. 5*c* illustrates a SAFT reconstructed image using a matched filter.

Synthetic aperture focusing of the compensated data set of FIG. 4a produces the image shown in FIG. 5c. The ideal image of the ring source would be a point surrounded by a fainter ring corresponding to the ring source diameter, as shown in FIG. 5a. The source used in this example is a ring of light which radiates sound outwards and inwards from the ring. The inward sound beam converges at the center of the ring and then radiates outward. Flaws outside the ring experience two sound pulses corresponding to the initial outward and inward components separated in time by an amount corresponding to the ring diameter. Correlation produces a match when the filter overlaps only the first pulse, both pulses, and only the second pulse. The overlap for both pulses is largest and is focused by the SAFT algorithm into the brighter middle point of FIG. 5c. The overlap for the first pulse or the second pulse corresponds to the fainter ring in FIG. 5c.

The SAFT image of the uncompensated scan data of FIG. 4b results in a compromised reconstruction which is focused only for a narrow range of frequencies, as shown in FIG. 5b. The low frequency components, which propagate more slowly for the dominant antisymmetric mode, are focused later into a broad "pedestal" 200 about the central point 202.

By contrast, the compensated data of FIG. 4b produce a SAFT image with significantly improved resolution and sensitivity, as shown in FIG. 5c. The benefits of synthetic aperture focusing following dispersion compensation include improved contrast, signal to noise ratio, and spatial localization of flaw signals, and increased sensitivity to small defects.

Figure 6:
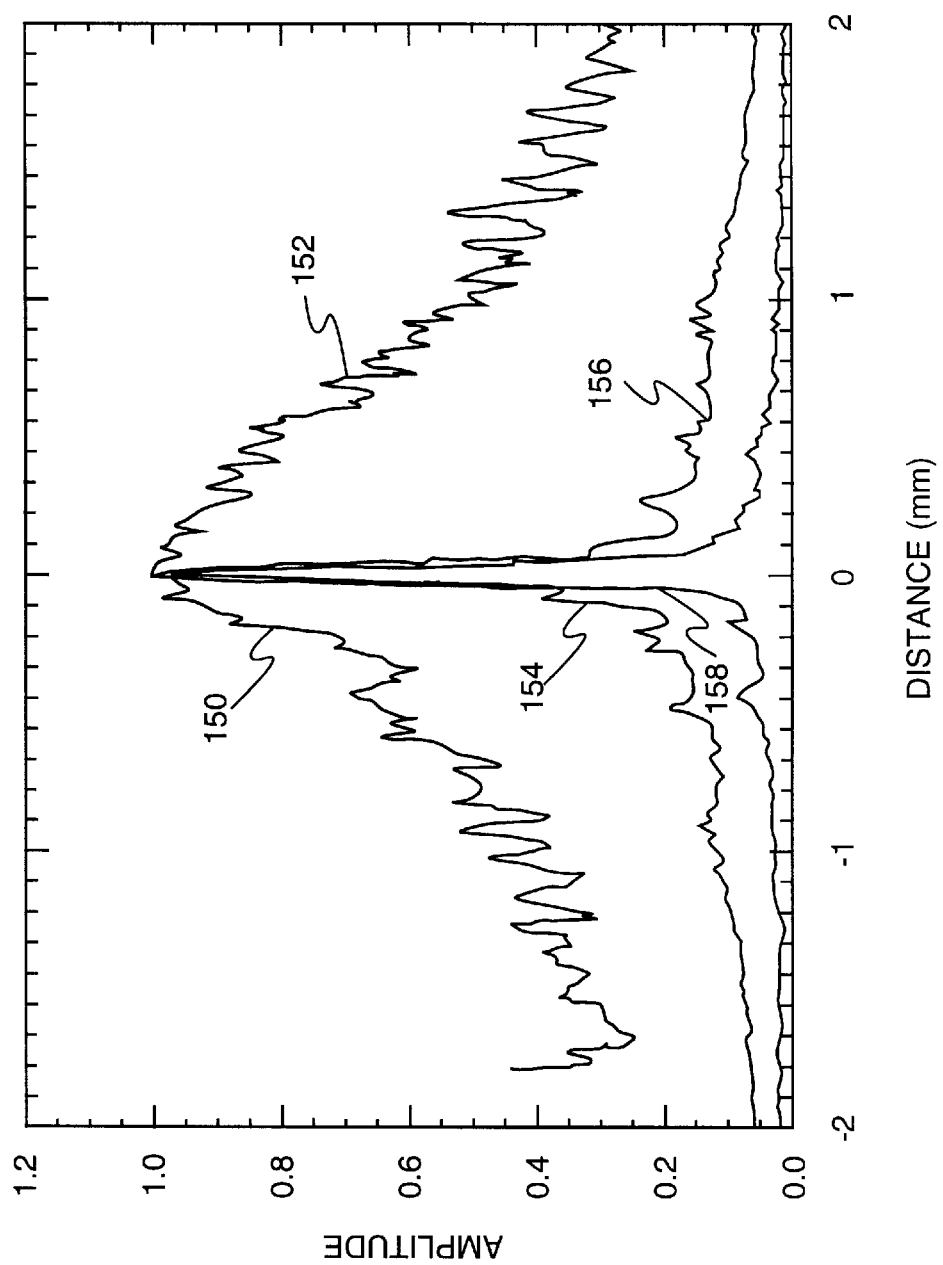
FIG. 6 illustrates the improved resolution which may be obtained with a matched filter and SAFT.

FIG. 6 is a graph of the maximum signal amplitude of the reconstructed images of FIGS. 5b–5c as a function of lateral position on the article. Plot 150 in FIG. 6 represents the signal amplitude of the uncompensated scan data. Plot 154 in FIG. 6 represents the signal amplitude through a center line of FIG. 5b. Plot 158 in FIG. 6 represents the signal amplitude through a center line of FIG. 5c. As shown in the figures, the uncompensated scan data 150 has no inherent focusing and produces a broad background 152 everywhere. SAFT focusing of the uncompensated scan data provides some enhancement, as shown in plot 154 and FIG. 5b but also introduces a raised background 156. SAFT focusing of the uncompensated scan data exhibits spreading of energy, which results in loss of sensitivity and resolution. SAFT focusing of the compensated data provides significant resolution enhancement and suppression of side lobes, as shown in FIG. 5c and plot 158. These images are indicative of the resolution of the imaging method and apparatus, also known as the one-way point spread function.

According to another embodiment of the invention, a matched filter can be constructed which is dependent on propagation distance and direction for an anisotropic material. In an anisotropic material, the velocity of sound is dependent upon the direction of propagation. The matched filter for an anisotropic material is constructed by measuring a response such as a surface displacement or velocity as a function of distance from the source and as a function of propagation direction. The matched filter which is a 3-dimensional matched filter, is applied in an analogous manner to remove dispersions in anisotropic materials which are dependent not only on distance but also on propagation direction. Rather than utilizing a single compensated waveform to image in all directions at a particular distance, each direction has a unique filter data point associated with it.

According to another embodiment of the invention, apodization of the synthetic aperture can be implemented, in which the data points representing the synthetic aperture are weighted differently to improve image resolution. For example, data points which represent measurements remote from the focal point can be weighted less than data points which represent measurements very close to the focal point. This technique improves accuracy by suppressing background noise and eliminating artifacts which arise near the edge of the aperture. Windowing functions such as the well-known Hanning window may be used to weight the various data points making up the synthetic aperture. Apodization may also be used, for example, to examine flaws in only a desired direction from a scan line, by zeroing data points in all but the desired direction.

According to another embodiment of the invention, the matched filter can be modified to filter all but a particular mode of propagation. In thin structures, it is common for one mode of propagation (e.g., the antisymmetric mode) to be more sensitive to a particular type of defect than other modes of propagation. Sensitivity can be quantified, for example, in terms of the amplitude of the reflected signal for a particular mode. A more sensitive mode of propagation for a particular type of defect has a greater reflected signal amplitude.

Modes of propagation which are less sensitive tend to decrease the resolution of the reconstructed image. To isolate the sensitive mode, the matched filter can be modified to filter all but the sensitive mode. For example, individual modes may be subtracted from the matched filter by first calculating them analytically and then subtracting them from the filter. Another method of subtracting individual modes involves frequency filtering the matched filter to suppress modes which exist only above certain frequencies. Temporal filtering may be used to suppress all modes faster than a certain velocity. For example, temporal filtering may be used to suppress all modes faster than the Rayleigh wave velocity, thereby suppressing all modes above the fundamental antisymmetric mode in an isotropic plate.

Isolation of individual modes with the matched filter also allows the reflectivity characteristics of a particular reflector to be evaluated. Defects vary by size, location within the part thickness, character (e.g. a hard imbedded particle, a crack, a water filled hole, etc.), etc. Different Lamb wave modes scatter off these defects with differing amplitudes and may mode convert to other modes. The data acquired for generating the matched filter can be used to obtain the dispersion relations for each of the propagating modes in the material, including complex materials such as composites or layered structures. These dispersion relations may be used to focus specific mode combinations of incident and reflected wave modes. A specific combination may be, for example, the fundamental asymmetric mode as a wave incident on a reflector, and the fundamental symmetric mode as the wave reflected off the reflector through mode conversion. By focusing the various mode combinations individually, the flaw reflectivity for each mode combination can be determined and quantified with a modal reflection coefficient. The modal reflection coefficients for a number of modes characterize a flaw and may be used to identify features of an unknown reflector, such as its depth within a part, what it is filled with, the distance between two faces of the flaw, etc.

To obtain a mode reflection coefficient for a particular incident/reflected mode combination, a matched filter is constructed in which all modes are subtracted except the mode or modes of interest. This process can be repeated for any desired combination of incident and reflected wave modes to create a reflectivity profile for a particular known defect. The reflectivity profile can then be correlated with the reflectivity profile of an unknown defect to characterize the unknown defect.

According to another embodiment of the invention, the source laser is modulated temporally and spatially to preferentially generate desired modes of propagation in the article, while suppressing other modes. Each mode of propagation can be represented as a line on a dispersion curve of frequency ($\omega=2\pi\nu$) versus wave number ($k=2\pi/\lambda$). To generate a particular mode, a point on the line is selected, representing a frequency and wave number. By temporally modulating the source laser, a particular frequency can be generated. By spatially modulating the source laser, a particular wavelength can be generated, for example by making the ring diameter of the source laser equal to the desired wavelength. The combination of frequency and wavelength selected generates the desired mode. Also, the laser source spot size influences the ultrasound beam spread in the object and can be tailored to match the desired aperture size and detection distance. The spot energy may be adjusted to vary the angular spread of ultrasound energy.

Exemplary embodiments of the invention may be used to quickly scan a thin structure such as an aircraft skin for defects and to construct a high resolution image thereof. In addition, the exemplary methods described herein can be combined with volumetric imaging techniques, such as those described in commonly-owned U.S. application Ser. No. 08/627,670, entitled Method and System for Laser Ultrasonic Imaging of an Object, by Lorraine et al, which is hereby incorporated by reference. For example, after forming an image of the article with surface and Lamb waves according to exemplary embodiments of the present invention, the above mentioned application can be used to generate 3D volumetric images with longitudinal and shear waves of particular regions of the article, such as those having defects. In this approach, the wavelength of the generated waves is decreased so that it is no longer the same order of magnitude as the thickness of the article. SAFT imaging can be used to focus at any desired depth in the article by arbitrarily setting the position of the focal point.

In volumetric imaging, longitudinal and transverse waves are generated which propagate through the volume of material. The longitudinal and transverse waves, like the different Lamb wave modes, travel at different velocities. Thus, a matched filter can be constructed which compensates for the different velocities of the longitudinal and transverse wave modes in an analogous manner to the matched filter which compensates for different Lamb wave modes.

Other modifications and improvements which may be implemented with exemplary embodiments of the invention include asymmetric apertures, in which the scan data points forming the aperture are not symmetric about the focal point, apertures with noncoincident sources and receivers, and multiple sources and/or receivers. Dynamic zooming of the aperture with depth may also be implemented, in which the size of the aperture or the number of data points forming the aperture increases as the image depth increases. As will be appreciated by those skilled in the art, exemplary embodiments of the invention provide a direct, efficient approach capable of imaging complex systems with multiple propagation modes or layers, which can be implemented in either the frequency or time domain.

Although the invention has been described with reference to exemplary embodiments, it will be appreciated that variations and modifications can be made by a person skilled in the art without departing from the scope and spirit of the invention.

What is claimed is:

1. A method of forming an image of an article comprising the steps of:
    propagating first waves in the article;
    measuring a response of the article to the first waves;
    forming a matched filter data set comprising first data points representing the response of the article to the first waves;
    generating second waves in the article at a plurality of generation positions on the article, which second waves propagate through the article;
    detecting a motion of the article at a plurality of detection positions to obtain second data points, the second data points forming a scan data set;
    multiplying the scan data set by the matched filter data set to generate a compensated data set comprising a plurality of third data points; and
    coherently summing the third data points in the compensated data set to form an image of the article.

2. The method of claim 1, wherein the first and second data points represent a surface displacement of the article as a function of time.

3. The method of claim 1, wherein the first and second data points represent a surface velocity of the article as a function of time.

4. The method of claim 1, wherein the matched filter data set contains information which compensates for propagation of multiple Lamb wave modes.

5. The method of claim 1, wherein the matched filter is a one-way matched filter.

6. The method of claim 1, wherein the matched filter is a pulse-echo matched filter.

7. The method of claim 6, wherein the pulse-echo matched filter is constructed with a reflector having reflective characteristics which simulate a defect in the article.

8. The method of claim 1, further comprising the step of reducing to zero a portion of the first data points of the matched filter data set.

9. The method of claim 8, wherein the portion of the first data points reduced to zero represents a mode of wave propagation.

10. The method of claim 1, wherein the matched filter data set contains information which compensates for frequency dispersion of the second waves.

11. The method of claim 1, further comprising the step of frequency filtering the matched filter to suppress modes which exist above a predetermined frequency.

12. The method of claim 10, wherein the second waves comprise Lamb waves.

13. The method of claim 1, further comprising the step of temporally filtering the matched filter to suppress modes having velocities greater than a predetermined velocity.

14. A method of forming an image of an article comprising the steps of:
    analytically deriving data points representing a response of the article as a function of the distance to a source;
    forming a matched filter data set comprising first data points representing the response of the article as a function of the distance to a source;
    generating waves in the article at a plurality of generation positions on the article, which waves propagate through the article;
    detecting a motion of the article at a plurality of detecting positions to obtain second data points, the second data points forming a scan data set;
    multiplying the scan data set by the matched filter data set to generate a compensated data set comprising a plurality of third data points; and
    coherently summing the third data points in the compensated data set to form an image of the article.

15. The method of claim 1, further comprising the steps of:
    forming the matched filter to comprise first data points representing the response of the article as a function of a direction to a source;

detecting the motion of the article at the plurality of detection positions for a plurality of directions to obtain the second data points, the second data points forming the scan data set; and multiplying the scan data set by the matched filter data set for a particular detection position and direction.

16. The method of claim 1, wherein the step of coherently summing the third data points in the compensated data set comprises:

calculating an adjusted distance for at least two detection positions based on a distance between a focal point and each of the at least two detection positions; and summing the third data points having adjusted distances which are about equal.

17. The method of claim 1, wherein the step of coherently summing the third data points in the compensated data set is carried out in three dimensions to form a 3-dimensional volumetric image of the article.

18. The method of claim 1, wherein the step of coherently summing the third data points is carried out in two dimensions with reference to a surface of the article.

19. The method of claim 1, wherein the step of coherently summing the third data points in the compensated data set comprises:

selecting a subset of the third data points in the compensated data set to define a synthetic aperture; and multiplying each of the third data points in the subset by a weighting factor based on a proximity of the respective third data point in the subset to a source.

20. The method of claim 1, wherein the step of coherently summing the third data points in the compensated data set comprises:

selecting a number of third data points in the compensated data set for coherent summing, the number based on a depth of a focal point, to form a subset which defines a synthetic aperture.

21. An apparatus comprising;

a wave generator for generating a wave in an article;

a detector for detecting a wave in the article; and a processor for:

sending first waves in the article;

measuring a response of the article to the first waves;

forming a matched filter based on the response of the article to the first waves;

directing the wave generator to generate second waves at a plurality of generation positions;

directing the detector to detect a motion of the article at a plurality of detection positions;

forming a scan data set from the detected motion of the article;

multiplying the scan data set by the matched filter to produce a compensated data set; and coherently summing data points in the compensated data set to produce a focused image.

22. The method of claim 1, wherein the step of generating waves in the article comprises directing a source laser emitting a source laser beam at a surface of the article.

23. The method of claim 1, wherein the step of generating waves in the article comprises generating Lamb waves.

24. The method of claim 1, wherein the step of generating waves in the article comprises generating longitudinal and transverse waves.

25. The apparatus of claim 21, wherein wave generator is adapted to generate a longitudinal wave and a transverse wave.

26. The apparatus of claim 21, wherein the wave generator comprises a first laser and the detector comprises a second laser.

27. The apparatus of claim 21, wherein wave generator is adapted to generate a Lamb wave.

28. The apparatus of claim 21, wherein the processor coherently sums the data points in the compensated data set by calculating a respective adjusted distance between a focal point and at least two of the detection positions and by summing the data points having adjusted distances which are about equal.

29. The apparatus of claim 21, wherein the detector is an interferometric detector.

* * * * *